United States Patent [19]
Cheung

[11] Patent Number: 5,862,806
[45] Date of Patent: Jan. 26, 1999

[54] BOROHYDRIDE REDUCTION OF BIOLOGICAL TISSUES

[75] Inventor: David Tai-Wai Cheung, Arcadia, Calif.

[73] Assignee: Mitroflow International, Inc., Canada

[21] Appl. No.: 961,342

[22] Filed: Oct. 30, 1997

[51] Int. Cl.⁶ .................................................. A61B 19/00
[52] U.S. Cl. .................................. 128/898; 623/2; 623/1; 623/11; 424/423; 8/94.11
[58] Field of Search .............................. 623/1, 2, 11, 66; 128/897, 898; 8/94.11; 424/422, 423

[56] References Cited

U.S. PATENT DOCUMENTS

| | | |
|---|---|---|
| 4,319,363 | 3/1982 | Ketharanathan . |
| 4,323,358 | 4/1982 | Lentz et al. . |
| 4,402,697 | 9/1983 | Pollock et al. . |
| 4,404,181 | 9/1983 | Mauthner . |
| 4,405,327 | 9/1983 | Pollock . |
| 4,553,974 | 11/1985 | Dewanjee . |
| 4,603,006 | 7/1986 | Sikes et al. . |
| 4,729,139 | 3/1988 | Nashef . |
| 4,776,853 | 10/1988 | Klement et al. . |
| 4,798,611 | 1/1989 | Freeman, Jr. . |
| 4,801,299 | 1/1989 | Brendel et al. . |
| 4,830,847 | 5/1989 | Benedict et al. . |
| 4,976,733 | 12/1990 | Girardot . |
| 5,002,566 | 3/1991 | Carpentier et al. . |
| 5,075,112 | 12/1991 | Lane . |
| 5,094,661 | 3/1992 | Levy et al. . |
| 5,104,405 | 4/1992 | Nimni . |
| 5,147,514 | 9/1992 | Mechanic . |
| 5,296,583 | 3/1994 | Levy . |
| 5,436,291 | 7/1995 | Levy et al. . |
| 5,437,287 | 8/1995 | Phillips et al. . |
| 5,447,536 | 9/1995 | Girardot et al. . |
| 5,476,516 | 12/1995 | Seifter et al. . |
| 5,507,810 | 4/1996 | Prewett et al. . |
| 5,595,571 | 1/1997 | Jaffe et al. . |
| 5,645,587 | 7/1997 | Chanda et al. . |

OTHER PUBLICATIONS

Amir Abolhoda, et al.; "Calcification of Bovine Preicardium: Glutaraldehyde Versus No–React Biomodification", (Ann Thorac Surg 1996; 62:169–74).
S.A. Archrekar, et al.; "A New Concept of Bioprosthetic Calcification", 1994, VI International Symposium Cardiac Bioprostheses, p. 119.
Eloisa Arbustini, et al.; "Modification by the Hancock T6 Process of Calcification of Bioprosthetic Cardiac Valves Implanted in Sheep", May 1, 1984, The American Journal of Cardiology, vol. 53, pp. 1388–1396.
Sophie Carpentier, et al.; "Heat Treatment Mitigates Calcification of Valvular Bioprostheses", 1997, VII International Symposiun Cardiac Bioprostheses, p. 127.
Jyotirmay Chanda, M.D.; "Prevention of Calcification of Heart Valve Bioprostheses: An Experimental Study in Rat", 1995; 60:S339–42, The Society of Thoracic Surgeons.
Suk Jung Choo, et al., "Influence of Shelf Life on The In Vitro Behavior of Bioprosthesis", 1997, VII International Symposium Cardiac Bioprostheses, p. 117.

M. Dahm, "Surface Seeding of Bioimplants With Homologous Cells Reduces Mineralisation of Biological Materials", 1994, VI International Symposium Cardiac Biprotheses, p. 121.
Weiliam Chen, et al.; Mechanism of Efficacy of 2–Amino Oleic Acid for Inhibition of Calcification of Glutaraldehyde–Pretreated Porcine Bioprosthetic Heart Valves, Jul. 1994, Circulation, vol. 90, No. 1, pp. 323–329.
Jean Marie Girardot, et al., "An Alternative to Glutaraldehyde Fixation for Biological Tissue", 1997, Biomedical Design and the Carlyle Fraser Heart Center, Atlanta, Georgia, Paper No. 9, p. 16.
M. Grabenwoge, e al., "Impact of glutaraldehyde on calcification of pericardial bioprosthetic heart valve material", Sep. 1996, Ann Thorac Surg, vol. 62.
M. G. Hazenkamp, et al., "The Value of The Stentless Biovalve Prosthesis: An Experimental Study", 1997, Paper No. 15, Dept. of Cardiothoracic Surgery, University Hospital Leiden, Leiden, The Netherlands, p. 23.
"Biotech companies target heart valve market", Biotechnology News, vol. 14, No. 7, p. 7.
Danielle Hirsch, et al., "Synergistic inhibition of the calcification of glutaraldehyde pretreated bovine preicardiun in a rat subdermal model by $FeCl_3$ and ethanehydroxydiphosphonate: pre–incubation and polymeric controlled release studies", 1993, Biomaterials, vol. 14, No. 9, pp. 705–711.
Danielle Hirsch, et al., "Effects of metallic ions and disphosphonates on inhibition on pericardial bioprosthetic tissue calcification and associated alkaline phosphatase activity", 1993, Biomaterials, vol. 14, No. 5, pp. 371–377.
W.R. Eric Jamieson, "Cardiac Valve Replacement Surgery: Prostheses and Technological Considerations", Surgical Technology International III, pp. 406–419.
R. C. Duhamel, et al., "Properties of Acellular Vascular Matrix", Apr. 27–May 1, 1984, Second World Congress on Biomaterials, Washington, D.C.
E. Jorge–Herrero, et al., "Influence of stress on calcification of delipidated bovine pericardial tissue employed in contruction of cardiac valves", 1996, Journal of Biomedical Materials Research, vol. 30, 411–415.

(List continued on next page.)

Primary Examiner—Mickey Yu
Assistant Examiner—Dinh X. Nguyen
Attorney, Agent, or Firm—Fulwider Patton Lee & Utecht, LLP

[57] ABSTRACT

A method of using sodium or potassium borohydride to reduce dehydrated, aldehyde treated biological tissues is disclosed. The method comprises the steps of: providing the tissue, such as porcine heart valves or bovine pericardium; treating the tissue with an aldehyde, such as glutaraldehyde; dehydrating the tissue, for example by treatment with an anhydrous polar organic solvent such as ethanol; and, treating the tissue with sodium or potassium borohydride. Following reduction, the sodium borohydride may be extracted from the tissue with an organic solvent, such as ethanol. The tissue may be rehydrated for use in bioprosthetic implants such as heart valves and pericardial patches.

20 Claims, No Drawings

OTHER PUBLICATIONS

E. Jorge–Herrero, et al., "Calcification of pericardial tissue pretreated with different amino acids", Mar. 1996, Biomaterials, vol. 17.

Robert J. Levy, et al., "Cardiovascular implant calcification: a survey and update", Oct. 1991, Biomaterials, vol. 12.

David J. Myers, et al., "A Comparison between Glutaraldehyde and Diepoxide–fixed Stentless Procine Aortic Valves: Biochemical and Mechanical Characterization and Resistance to Mineralizalion", 1995, The Journal of Heart Valve Diesease, vol. 4, Suppl. I.

E. A. Nemets, et al., "An N–substituted polyurea coating with high affinity for heparin", Jul.–Sep. 1993, BBH, vol. 39.

Christoher A. Pereira, et al., "Effect of alternative crosslinking methods on the low strain rate viscoelastic properties of bovine percardial bioprosthetic material", 1990, Journal of Biomedical Materials Research, vol. 24, pp. 345–361.

H. Petite, et al., "Use of the acyl azide method for cross–linking collagen–rich tissues such as pericardium", 1990, Journal of Biomedical Materials Research, vol. 24, pp. 179–187.

H. Petite, et al., "Use of diphenylphosphorylazide for cross–linking collagen–based biomaterials", 1994, Journal of Biomedical Materials Research, vol. 28, pp. 159–165.

F. J. Shoen, et al., "Bioprosthetic heart valve calcification: membrane–mediated events and alkaline phosphatase", 1992, Bone and Mineral, pp. 129–133.

Frederick J. Schoen, et al., "Antimineralization treatments for bioprosthetic heart valves", Nov. 1992, The Journal of Thoracic and Cardiovascular Surgery, vol. 14, No. 5, pp. 1285–1288.

Armin Schroll, "Minimal Calcium Uptake With Improved Mechanical Durabaility of A Porcine Bioprosthesis After Post–Fixation With Aminopentane", 1997, VII International Symposium Cardiac Bioprostheses, p. 122.

J.M. Van Gelder, et al., "Anticalcification and antiresorption effects of bisacylphosphonates", Bone, 1995 May, 16:5.

N. Vyavahare, et al., "Ethanol and Aluminum Chloride Pre–Incubation to Inhibit Bioprosthetic Heart Valve Calcification", 1997, VII International Symposium Cardiac Bioprostheses, p. 124.

T. Walther, et al., "Anticalcification treatments for stentless bioprostheses", 1997, VII International Symposium Cardiac Bioprostheses, p. 126.

Peter Zilla, et al., "Improved Ultrastructural Preservation of Bioprosthetic Tissue", 1997, VII International Symposium Cardiac Bioprostheses, p. 116.

Weiliam Chen, et al., "Effect of 2–amino oelic acid exposure conditions on the inhibition of calcification of glutraldehyde cross–linked procine aortic valves", 1994, Journal of Biomedical Materials Research, vol. 28, pp. 1485–1495.

Jyotirmay Chanda, et al., "Prevention of Calcification of Tissue Valves", 1994, Artificial Organs, vol. 18, No. 10, pp. 752–757.

Olga Bayliss, C.W. Adams, The pH dependence of borohydride as an aldehyde reductant, Histochemical Journal, 11 (1979), 111–116.

L. Delbridge, A.V. Everitt, M.G. Steele, The effect of acid phosphate on the solubility of collagen, Connective Tissue Research, 1972, vol. 1, pp. 311–314.

Linda Brown, Margaret Harkness, R.D. Harkness, Effect of hydrazine and other aldehyde reacting agents on mechanical properties on rat tail skin, Acta Physiol. (1969), 36(1–2), 157–69.

Marvin Tanzer, Collagen crosslinks: stabilization by borohydride reduction, Biochimica et biophysica acta, 133 (1967), 584–587.

Katharyn Hey, C. M. Lachs, et al., Crosslinked Fibrous Collagen for use as a Dermal Implant: Control of the Cytotoxic Effects of Glutraldehyde and Dimethylsuberimidate, Biotechnology and Applied Biochemistry 12, 85–93 (1990).

BOROHYDRIDE REDUCTION OF BIOLOGICAL TISSUES

FIELD OF INVENTION

The invention is in the field of processes for preparing biological tissues of extracellular matrices for implantation as bioprosthetic implants. The invention relates to a process for using sodium or potassium borohydride to modify reactive chemical groups in biological tissues or protein matrices that have been cross-linked or treated by aldehydes or other chemical reagents.

BACKGROUND

Treatment of biological tissues with glutaraldehyde is a preferred method for manufacturing bioprosthetic implants. Glutaraldehyde forms cross-links and polymers with a variety of matrix components of biological tissues, rendering these tissues less immunogenic when implanted in a living host. Glutaraldehyde cross-linking also alters the mechanical properties of biological tissues.

Glutaraldehyde cross-linked porcine heart valves and bovine pericardial tissues have been used as material for bioprosthetic human heart valves. Glutaraldehyde treated blood vessels and pericardial patches have also been used in other applications.

Glutaraldehyde treated biological tissues, especially porcine heart valves and bovine pericardial tissues, have been used as materials for bioprosthetic heart valves for more than 20 years. It has become evident that calcification of the glutaraldehyde treated bioprosthetic heart valves has been a major cause of long term device failure.

The exact mechanism underlying the calcification of glutaraldehyde treated heart valves is not known. It has been suggested that the toxicity of the glutaraldehyde polymers or the breakdown products of the glutaraldehyde polymers cause the death of connective tissue cells arriving at the implant site. The remnants of these dead cells may then act as nidi for the nitiation of calcificaiton. The toxicity of the glutaraldehyde polymers which leach out to tissue surrounding a glutaraldehyde cross-linked bio-implant may, through a similar mechanism, further complicate the integration of the implant into the host tissue. The free aldehyde groups of the glutaraldehyde polymers may contribute to the toxicity of the polymers.

A variety of approaches have been taken to counteract calcification of glutaraldehyde treated implants. For example, aldehyde treated tissues have been reacted with polyols (U.S. Pat. No. 5,476,516, issued to Seitter et al., 19 Dec. 1995), treated with alipathic carboxylic acids (U.S. Pat. No. 4,976,733 issued to Girardot 11 Dec, 1990) treated with partially degraded heparin (U.S. Pat. No. 5,645,587 issued to Chanda et al. 8 Jul. 1997), treated with sodium dodecyl sulfate (U.S. Pat. No. 4,323,358 issued to Lentz et al. 6 Apr. 1982), treated with polysaccharides, disphsphonates or phosphoproteins (U.S. Pat. No. 5,104,405 to Nimni 14 Apr. 1992), impregnated with ferric or stannic salts (U.S. Pat. No. 5,002,566 to Carpentier et al. 26 Mar. 1991), and treated with trivalent aluminum cations (U.S. Pat. No. 5,094,661 to Levy et al. 10 Mar. 1992).

Sodium borohydride in aqueous solution is a known reducing agent. Sodium borohydride in solution has previously been used as a reducing agent to treat glutaraldehyde fixed tissues. U.S. Pat. No. 4,553,974 issued to Dewanjee on 19 Nov. 1985 discloses a process for treatment of glutaraldehyde fixed tissue with a calcification inhibiting agent, and then reducing the tissue with sodium borohydride. The calcification inhibiting agent contains reactive amino groups that bond to free reactive groups in the fixed tissue. Dewanjee '974 discloses a variety of amino diphosphonate compounds as effective calcification inhibiting agents (as do U.S. Pat. Nos. 5,296,583 and 5,436,291 issued to Levy et al. on 22 Mar. 1994 and 25 Jul. 1995 respectively). Dewanjee '974 teaches that a solution of sodium borohydride may be used to stabilize the bonding of such amino diphosphonates and glutaraldehyde to protein molecules.

Chen et al. ("Effect of 2-amino oleic acid exposure conditions on the inhibition of calcification of glutaraldehyde cross-linked porcine aortic valves" Journal of Biomedical Materials Research, Vol. 28, 1485–1495 (1994)) teach that the use of a sodium borohydride solution alone to treat glutaraldehyde fixed aortic tissues is not effective to reduce calcification in the rat subdermal implant model. In fact, when used on aortic wall tissue, the sodium borohydride treatment resulted in increased calcification compared to controls with no treatment.

SUMMARY OF THE INVENTION

The invention provides a method of preparing biological tissue that includes the following steps:

(1) providing a biological tissue having reactive groups that will react with an aldehyde. The biological tissue may be fibrous material derived from animal origins, such as mammalian pericardium.

(2) Treating the biological tissue with an aldehyde, such as glutaraldehyde or other polymeric forms of aldehydes, or polymers containing aldehydes and/or ketones. Biological tissues containing collagen and other proteins may be cross-linked by such treatment. Following such treatment, the tissue typically includes substituents such as aldehyde groups and Schiff's bases.

(3) Dehydrate the biological tissue. The tissue may be dehydrated by treating it with a polar organic solvent, such as ethanol, increasingly anhydrous solutions of the polar organic solvent may be used for this purpose.

(4) Treating the tissue with sodium or potassium borohydride in a polar organic solvent at a pH of less than about 8 to reduce substituents on the tissue such as free aldehyde groups and Schiff bases.

Additional steps may be useful:

Following treatment of the tissue with the borohydride, the borohydride may be removed from the tissue. Removal of the borohydride may be accomplished by extraction into an appropriate organic solvent (such as ethanol, other alcohols, acetonitrile or pyridine). Removal of the hydride from the tissue may be used to stop the reduction reaction.

To prepare tissue treated in accordance with the invention for use, the tissue may be rehydrated. For example, the tissue may be treated with increasingly dilute concentrations of a polar organic solvent in aqueous solution.

The concentration of reactants, pH, temperature of reaction and duration of reaction are all parameters of the process of the invention that may be varied by those skilled in this art in order to vary the results achieved with the process of the invention. Generally, the reduction should be carried out at temperatures below those which can cause macromolecules in the tissue to loose their tertiary and quaternary structures. The reduction may preferably be carried out for a sufficient period of time, and under appropriate conditions, to reduce substantially all of the aldehydes and Schiff's bases in the tissue. A quantity of borohydride may be used that is approximately stoichiometrically equivalent to the theoretical amount of aldehydes and Schiff bases in the tissue. The borohydride may be provided in an amount that exceeds the saturation concentration of the borohydride in the polar organic solvent. Providing such an excess of borohydride may help to ensure that there is a continual supply of the sodium borohydride as the reduction reaction progresses.

In a preferred embodiment, dehydration may be performed in a stepwise procedure by immersing the biological tissues in a series of solutions with increasing concentrations of alcohol (or other polar organic solvents) in water, or in a continuously concentrating solvent solution, such as a gradient solution system. As the final dehydration step, the tissues may be immersed in 100% alcohol. The alcohol may be aspirated away from the tissue and a solution of sodium borohydride in 100% alcohol added to the dehydrated biological material. Reduction of the tissues with borohydride may be allowed to proceed at 4° C. for approximately 24 hours (overnight), fresh sodium borohydride in ethanol solution may then be added and the reaction continued at 4° C. for a further period of approximately 24 hours (overnight). The borohydride solution may then be aspirated away from the tissues. The excess borohydride in the tissue may be extracted by washing the tissues in 100% alcohol. The borohydride reduced material may then be rehydrated by immersing the material in a series of alcohol solutions with decreasing concentrations of alcohol in water.

The process of the present invention reduces the aldehyde groups in an aldehyde treated biological tissue to improve the biocompatability of the tissue. Although the process uses a strong reducing agent, sodium or potassium borohydride, the structural integrity of the tissues is preserved, as evidenced by the results disclosed herein. Accordingly, use of the borohydride in accordance with the process of the invention does not appear to adversely affect structural components of the tissues. However, if borohydride is used to reduce tissues in methods which differ from the process of the present invention, adverse effects on the structural components of the tissues, such as collagen, elastin or proteoglycan, may occur.

The process of the invention has the additional advantage of stabilizing the potentially reversible Schiff's base cross-links between the aldehyde and the treated tissues, for example between glutaraldehyde polymers and protein components of the tissue. It has been shown that glutaraldehyde cross-linked biological tissues release toxic components to cells in vitro even after extensive and prolonged washing (up to 6 months). This is evidence that the attachment of glutaraldehyde or its polymers to tissue fibers is reversible. The reversibility of the reaction is counteracted by reducing the Schiff's bases. This reduction, converting the C↑N double bond to a C–N single bond also increases the rotational freedom of the glutaraldehyde polymer which is attached to the tissue fibre. This aspect of the reduction of the Schiff's bases may underlie another unanticipated advantage of the invention: the glutaraldehyde cross-linked biological tissue after reduction has a compliance characteristic closer to native tissue than non-reduced tissue.

Biological tissues reduced in accordance with the invention may be used as implanted materials, such as heart valve prostheses, patches or conduits. In addition, such tissues may be used in other biological processes, including instrumentation and biological test support materials.

DETAILED DESCRIPTION

Glutaraldehyde treated bovine pericardia were prepared by immersing freshly harvested pericardial tissue in glutaraldehyde solution in phosphate buffered saline for several days. The glutaraldehyde tissues were dehydrated by immersing the tissues in 25% ethanol in water (tissue: volume=5 g wet weight: 100 ml) for 15 minutes the 25% ethanol was aspirated and a 50% ethanol solution was added. After 15 minutes the 50% ethanol was aspirated and a 75% ethanol was added. After another 15 minutes the 75% ethanol was aspirated and 100% ethanol was added. In the same manner the 100% ethanol was aspirated and replaced by new 100% ethanol two additional times.

Those skilled in the art of this invention will understand that there are a variety of ways in which a tissue may be dehydrated in accordance with this invention. The dehydration step should preferably remove as much water as possible, since the presence of water will interfere with the aldehyde reduction reaction. The tissue may be dehydrated by treating it with polar organic solvents other than ethanol, such as other alcohols like isopropanol (because of their physical properties, methanol and alcohols with more than four carbons would generally not be practical as the major constituents of the dehydrating agent), acetonitrile, pyridine or mixtures of such solvents. Such solvents may be selected in accordance with the present invention by virtue of their ability to extract water from the treated tissue, while not reacting adversely with the tissue. Increasingly anhydrous solutions of the polar organic solvent may be used for this purpose. In each case, it will be appreciated that the efficacy of the dehydrating agent may be tested according to its ability to dry the tissue while not interfering with the other aspects of the process of the invention.

Dehydration of glutaraldehyde treated tissues prior to reduction with borohydride is an important aspect of the invention. Sodium or potassium borohydride may reduce aldehydes, Schiff's bases and similar functional groups in aqueous solution and neutral pH. However, under these conditions, the borohydrides are very labile and are themselves readily hydrolyzed by water. Another difficulty is that such a reduction reaction generates hydrogen gas as a by-product which can be trapped in the tissue matrices. As the trapped gas accumulates as bubbles in the matrices, the bubbles may disrupt the tissue matrices as well as create physical voids. They may also create physical barriers for fluid diffusion, preventing reduction agents from entering the tissue. In addition, bubbles may make it difficult for reduction by-products to diffuse out of the tissue, thus causing a rise of the pH in the micro environment inside the tissue. When the pH of a borohydride solution rises above 8, cleavage of peptide bonds may occur. The cleavage of peptide bonds would significantly weaken the tissue's fibrous structure. It is therefore important to control the pH environment of the reduction reaction and prevent the formation of trapped hydrogen gas bubbles.

To initiate the reduction reaction, the 100% ethanol is aspirated and sodium or potassium borohydride reduction reagent added. In a preferred embodiment, the reduction reagent may be prepared by adding 0.2 grams of sodium borohydride to 100 ml of 100% ethanol. The reduction reaction may be allowed to continue at 4° C. for approximately 24 hours (overnight). Fresh reduction reagent may then be added and the reaction continued at 4° C. for a further period of approximately 24 hours (overnight). It will be appreciated that the duration and conditions of the reduction reaction are preferably sufficient to ensure that substantially all of the free aldehydes in the tissue are reduced.

To control pH in accordance with the present invention during the reduction reaction, the pH of the reducing reaction solution may be monitored. If the pH rises to 8 or above, the sodium borohydride solution may be removed and replaced with a fresh solution of sodium borohydride (preferably sodium borohydride in ethanol).

At the end of the reduction reaction, the reduction reagent may be aspirated and 100% ethanol used to wash the tissues for 15 min. The washing procedure may be repeated two more times. The washed tissues were re-hydrated by removing the 100% ethanol by aspiration and adding a 75% ethanol solution. Fifteen minutes later, the 75% ethanol was aspirated and a 50% ethanol solution was added. The reduced tissues were then stored in 50% ethanol.

For use, the tissue treated in accordance with the method of the invention may be sterilized. The tissue may also be treated with heparin, for example by dipping in a heparin bath. In one embodiment, the tissue is sterilized and then treated with heparin.

In accordance with known techniques for using glutaraldehyde fixed tissues, tissues treated in accordance with the invention may be fashioned into a variety of bioprosthetic implants, such as heart valves and pericardial patches.

For evaluation of the reduced tissues by in vitro and in vivo tests, as disclosed below, tissue samples were immersed and rinsed in phosphate buffered saline at 4° C. for 15 min. The reduced tissues appear white and very flexible, unexpectedly resembling fresh non-glutaraldehyde treated tissues.

The effectiveness of the reduction reaction in reducing free aldehydes was determined by immersing a piece of the reduced tissue in Fuchsin-sulfite reagent (Schiff's reagent) for 15 min. Non-reduced tissues turn pink and purple quickly. Reduced tissue samples remain white and turned slightly pink after one hour, indicating that the concentration of free aldehydes in the tissue had been substantially reduced.

The integrity of collagen fibers in the reduced tissues was tested by several methods. The first method evaluated the quarter scattered banding of collagen fibers using transmission electron microscopy. Reduced tissues were dehydrated and embedded in epoxy resin directly prior to sectioning and staining. The resulting electron micrographs show that the collagen fibers in the reduced tissues were intact since the banding pattern appeared normal.

The second method was to compare the shrink temperature of the reduced samples with that of the native fresh tissues as well as tissues cross-linked with glutaraldehyde but not reduced. Tissues were sandwiched between two glass slides (using the glass slides as support) and immersed in physiological 0.9% saline. The saline was gradually heated at approximately 1° C. per minute. The length of the tissue strips were measured at frequent intervals. The exact temperature at which the tissue's shrinkage rate was at least 1 mm/min was recorded as the shrink temperature. From this inflection point on a tissue length vs. temperature graph the shrinkage rate increases dramatically. The results show that the shrink temperature of the reduced tissues was $79.4°\pm0.3°$ C. compared to $83.7°\pm0.2°$ C. for the non-reduced cross-linked tissues and $62.3°\pm0.5°$ C. for the fresh native tissues. These results provide evidence that the collagen fibers as well as the bulk of the glutaraldehyde cross-links remain intact following reduction of the tissue.

The mechanical properties of the reduced tissues were examined by two different methods. In the first method, dumb-bell shaped tissues were stamped from pericardial tissues treated by glutaraldehyde and post-glutaraldehyde reduction. The tissues were pulled on an Instron Instrument at a load speed of 10 mm/minute. The results in Table 1 show that there is no significant difference between the stress/strain ratios of the two groups. There is also no difference in the maximum load strength of the two groups. In the second method, tissues were pulled to 2.5 kg and held at that distance for 15 min. while the reduction in load was measured. The result in Table 2 shows that the initial slope of the relaxation curves of the two sample groups were not significantly different. These results indicate that the post-glutaraldehyde reduction process did not alter or weaken the mechanical properties of the tissues.

The biocompatibility of the glutaraldehyde treated bovine pericardium after reduction by borohydride was examined in tissue culture studies. Reduced and non-reduced tissues were cut into round disks which fit snugly in the wells of a multi-well tissue culture plate. After the tissues were washed insaline for four weeks with frequent change of saline, the tissues were sterilized with 70% ethanol and washed in sterile saline again prior to being placed in the tissue culture wells and held to the bottom of the wells by Teflon inserts. Culture medium was added and bovine cornea endothelial cells and human foreskin fibroblasts were separately added to different wells containing the tissues. One week after the cells were seeded, tissue culture medium was removed and a 2% glutaraldehyde solution was added to each well to fix the cells. Tissues were then carefully lifted from the culture wells and processed for scanning electron microscopy and transmission electron microscopy. The electron micrographs showed that both human fibroblasts and bovine endothelial cells attached and grew on the reduced as well as fresh untreated tissues with morphology and characteristics of the corresponding cell types. On the contrary, cells did not grow well on tissues cross-linked by glutaraldehyde but not reduced.

In a parallel experiment, $^3$H-proline was added to the culture medium for 24 hours after the initial one-week incubation. At the end of the 24-hour period, the medium was removed and the tissues were washed with 4M saline to remove free radioactivity while keeping the collagen in the precipitated form. The amount of radioactivity remaining in the tissues, which reflects the amounts of $^3$H-collagen synthesized by the cells attached to the tissues, was measured by scintillation counting. The results in Table 3 show that the human fibroblasts on all tissue groups (glutaraldehyde cross-linked only, post-glutaraldehyde reduction and fresh) did not synthesize much collagen. On the other hand, bovine endothelial cells synthesized significant amounts of collagen on both the fresh and reduced tissues but minimal amounts on glutaraldehyde treated tissues. These results show that the reduction method of the invention reduced the cytotoxicity of the tissues as a result of glutaraldehyde cross-linking. As a result, both fibroblasts and endothelial cells can attach and proliferate on the tissues.

Although both fibroblasts and endothelial cells were attaching and growing on the reduced tissues, they did not behave in the same manner. While endothelial cells produced significant amounts of collagen necessary to strengthen the adhesion of endothelial cells on the matrices, fibroblasts were not found to produce large amounts of collagen which could lead to fibrosis or excess amount of granulation tissues adjacent to the implants.

In a rat subdermal study, calcium analysis revealed that after eight weeks implantation reduced bovine pericardial tissues contained $2.12\pm2.03$ $Ca^{++}$ mg/g, compared to $09.90\pm43.26$ $Ca^{++}$ mg/g in non-reduced glutaraldehyde fixed bovine pericardial tissue. This result indicates that the post-glutaraldehyde reduction process is surprisingly effective in mitigating tissue calcification in the rat model. These results are in direct contrast to the results reported by Chen et al., in which the use of sodium borohydride alone is ineffective in mitigating calcification of glutaraldehyde cross-linked tissues ("Effect of 2-amino oleic acid exposure conditions on the inhibition of calcification of glutaraldehyde cross-linked porcine aortic valves" Journal of Biomedical Materials Research, Vol. 28, 1485–1495 (1994)). There is no indication in Chen et al. that their treatment included dehydrating the tissues, nor that their sodium borohydride reduction was carried out in a polar organic solvent, nor that pH was controlled during reduction. These are all factors which may have affected the result obtained by Chen et al.

In the rat subdermal study, histological analysis of treated tissues by light microscopy observed the usual foreign body giant cell and histocytic reaction (macrophages present in connective tissues at the sites of the implants), but there was no evidence of necrosis or fatty infiltration, and only a small number of cases showing a moderate degree of chronic inflammation at the junction of the implants.

In the following tables, G only—Glutaraldehyde fixed only; PGR=Post-glutaraldehyde treated.

TABLE 1

STRESS-STRAIN TEST

| Tissues | # of Samples | Max. Load (kg) ± standard deviation | Stress/Strain (kg/mm) ± standard deviation |
|---|---|---|---|
| G only | 9 | 7.04 ± 2.2 | 0.56 ± 0.16 |
| PGR | 9 | 7.4 ± 1.62 | 0.51 ± 0.14 |

TABLE 2

STRESS RELAXATION TEST

| Tissues | # of Samples | Relaxation curve Slope (g/min) ± standard deviation |
|---|---|---|
| G only | 5 | 8.3 ± 1 |
| PGR | 3 | 8.8 ± 1 |

TABLE 3

$^3$H-COLLAGEN SYNTHESIS STUDY WITH FIBROBLAST CELLS

| Tissue | # of Samples | Attached Radioactivity (cpm/well) Fibroblast Cells |
|---|---|---|
| G only | 3 | 3840 |
| PGR | 3 | 3969 |
| Untreated Tissue | 3 | 3793 |

TABLE 4

$^3$H-COLLAGEN SYNTHESIS STUDY WITH ENDOTHELIAL CELLS

| Tissues | # of Samples | Attached Radioactivity (cpm/well) Endothelial Cells |
|---|---|---|
| G only | 3 | 6771 |
| PGR | 3 | 10077 |
| Untreated Tissue | 3 | 20666 |

As will be apparent to those skilled in the art in light of the foregoing disclosure, many alterations and modifications are possible in the practice of this invention without departing from the spirit or scope thereof. It will be appreciated that the testing methods and assays disclosed herein provide methods for evaluating various aspects of the process of the invention. Parameters such as reaction times and temperatures, choice of polar organic solvent and selection of aldehyde fixative may be varied in accordance with the invention, and the results of such variations assayed as disclosed herein to determine optimal and operative embodiments of the invention, and to avoid inoperative processes which are not encompassed by the present invention. Accordingly, the scope of the invention is to be construed in accordance with the substance defined by the following claims.

I claim:

1. A method of preparing biological tissue comprising the steps of:
    a. providing a biological tissue having reactive groups that will react with an aldehyde;
    b. treating the biological tissue with the aldehyde, reacting the aldehyde with the reactive groups, producing substituents on the tissue selected from the group consisting of free aldehyde groups, Schiff's bases, and combinations thereof;
    c. dehydrating the tissue; and,
    d. treating the tissue with a borohydride, selected from the group consisting of sodium and potassium borohydride, in a polar organic solvent at a pH of less than about 8 to reduce the substituents on the tissue.

2. The method of claim 1 further comprising the step of washing the tissue with the polar organic solvent to remove the borohydride from the tissue.

3. The method of claim 2 further comprising the step of rehydrating the tissue.

4. The method of claim 1 wherein the biological tissue is selected from the group consisting of mammalian pericardium, mammalian heart valves and mammalian vascular grafts.

5. The method of claim 1 wherein the aldehyde is glutaraldehyde and the polar organic solvent is ethanol.

6. The method of claim 1 wherein the step of dehydrating the tissue comprises the step of treating the tissue with the polar organic solvent.

7. The method of claim 6 wherein the polar organic solvent is selected from the group consisting of ethanol, isopropanol, acetonitrile and pyridine.

8. The method of claim 7 wherein the step of treating the tissue with a polar organic solvent comprises treating the tissue with increasingly anhydrous solutions of the polar organic solvent.

9. The method of claim 1 wherein the step of treating the tissue with a borohydride is carried out under anhydrous conditions.

10. The method of claim 3 wherein the step of rehydrating the tissue comprises treating the tissue with increasingly dilute concentrations of the polar organic solvent in aqueous solution.

11. The method of claim 1, further comprising the step of sterilizing the biological tissue.

12. The method of claim 11, further comprising the step of treating the tissue with heparin.

13. The method of claim 1, further comprising the step of using the tissue to make a bioprosthetic implant.

14. The method of claim 1 wherein the borohydride is sodium borohydride.

15. A method of preparing biological tissue comprising the steps of:
    a. providing a dehydrated biological tissue having substituents selected from the group consisting of free aldehyde groups, Schiff's bases, and combinations thereof; and, b. treating the tissue with a borohydride, selected from the group consisting of sodium borohydride and potassium borohydride, in a polar organic solvent at a pH of less than about 8 to reduce the substituents.

16. The method of claim 14 further comprising the step of washing the tissue with the polar organic solvent to remove the borohydride from the tissue.

17. The method of claim 15 further comprising the step of rehydrating the tissue.

18. The method of claim 14 wherein the borohydride is sodium borohydride.

19. The method of claim 14 wherein the polar organic solvent is selected from the group consisting of ethanol, isopropanol, acetonitrile and pyridine.

20. The method of claim 19 wherein the polar organic solvent is ethanol.

* * * * *

UNITED STATES PATENT AND TRADEMARK OFFICE
CERTIFICATE OF CORRECTION

PATENT NO. : 5,862,806
DATED : Jan. 26, 1999
INVENTOR(S) : David Tai-Wai Cheung

It is certified that error appears in the above-identified patent and that said Letters Patent is hereby corrected as shown below:

Title page: under OTHER PUBLICATIONS, line 1 of text, change "Preicardium", to read --Pericardium--.

Title page: under OTHER PUBLICATIONS, second column, line 23 of text, change "preicadiun", to read --Pericardium--.

Title page: under OTHER PUBLICATIONS, second column, 2 lines from end of text, change "contruction", to read --construction--.

Page 2 under OTHER PUBLICATIONS, first column, line 7 of text, change "Procine", to read --Porcine--.

Page 2 under OTHER PUBLICATIONS, first column, line 9 of text, change "Mineralizalion", to read --Mineralization--..

Page 2 under OTHER PUBLICATIONS, first column, line 10 of text, change "Diesease", to read --Disease--.

Page 2 under OTHER PUBLICATIONS, first column, line 14 of text, change "Christoher", to read --Chistoper--.

Page 2 under OTHER PUBLICATIONS, first column, line 16 of text, change "percardial", to read --pericardial--.

Page 2 under OTHER PUBLICATIONS, first column, 5 lines up from the bottom text, change "Durabaility"", to read --Durability--.

UNITED STATES PATENT AND TRADEMARK OFFICE
CERTIFICATE OF CORRECTION

PATENT NO. : 5,862,806
DATED : Jan. 26, 1999
INVENTOR(S) : David Tai-Wai Cheung

Page 2 of 3

It is certified that error appears in the above-identified patent and that said Letters Patent is hereby corrected as shown below:

Page 2 under OTHER PUBLICATIONS, second column, line 12 of text, change "glutraldehyde", to read --glutaraldehyde--.

Page 2 under OTHER PUBLICATIONS, second column, line 13 of text, change "procine", to read --porcine--.

Page 2 under OTHER PUBLICATIONS, second column, 3 lines up from bottom text, change "Glutraldehyde", to read --Glutaraldehyde--.

Column 1, line 40, change "nitiation of calcificaiton", to read --initiation of calcification--.

Column 1, line 56, change "disphsphonates", to read --diphosphonates--.

Column 3, line 51, change "C↑N", to read --C=N--.

Column 6, line 16, change "insaline", to read --in saline--.

Column 6, line 62, change "09.90", to read --89.98--.

UNITED STATES PATENT AND TRADEMARK OFFICE
CERTIFICATE OF CORRECTION

PATENT NO. : 5,862,806
DATED : Jan. 26, 1999
INVENTOR(S) : David Tai-Wai Cheung

It is certified that error appears in the above-identified patent and that said Letters Patent is hereby corrected as shown below:

Column 7, line 13, change "histocytic", to read --histiocytic--.

Column 7, TABLE 4, line 62, change "10077", to read --18077--.

Signed and Sealed this

Seventeenth Day of August, 1999

Attest:

Attesting Officer

Q. TODD DICKINSON

Acting Commissioner of Patents and Trademarks